US011485925B2

United States Patent
Frankson et al.

(10) Patent No.: US 11,485,925 B2
(45) Date of Patent: Nov. 1, 2022

(54) LUBRICOUS SILICONE

(71) Applicant: Cardiac Pacemakers, Inc., St. Paul, MN (US)

(72) Inventors: Danielle Frankson, Dayton, MN (US); Joel T. Eggert, Plymouth, MN (US); Poorva Rajguru, New Brighton, MN (US); Kate Jensen, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 166 days.

(21) Appl. No.: 16/683,482

(22) Filed: Nov. 14, 2019

(65) Prior Publication Data

US 2020/0157455 A1 May 21, 2020

Related U.S. Application Data

(60) Provisional application No. 62/768,607, filed on Nov. 16, 2018.

(51) Int. Cl.
*C10M 107/44* (2006.01)
*C08J 7/04* (2020.01)
*A61L 29/08* (2006.01)
*A61L 29/14* (2006.01)
*C10N 40/00* (2006.01)
*C10N 50/08* (2006.01)

(52) U.S. Cl.
CPC ......... *C10M 107/44* (2013.01); *A61L 29/085* (2013.01); *A61L 29/14* (2013.01); *C08J 7/0427* (2020.01); *A61L 2400/10* (2013.01);
(Continued)

(58) Field of Classification Search
CPC ........ A61L 29/02; A61L 29/085; A61L 29/14; A61L 2400/10; A61L 2400/18;
(Continued)

(56) References Cited

U.S. PATENT DOCUMENTS

| 4,312,693 A * | 1/1982 | Salensky ............... C08J 7/0427 156/272.2 |
| 6,197,051 B1 * | 3/2001 | Zhong .................. A61L 33/062 427/2.25 |
| 7,221,982 B2 * | 5/2007 | Aron ....................... A61B 5/283 607/116 |

(Continued)

FOREIGN PATENT DOCUMENTS

| CN | 1261288 A | 7/2000 |
| CN | 103132045 A | 6/2013 |
| CN | 104558666 A | 4/2015 |
| KR | 10-2012-0079902 A | 7/2012 |

OTHER PUBLICATIONS

Desmet, T., Morent, R., De Geyter, N., Leys, C., Schacht, E., Dubruel, P., "Nonthermal Plasma Technology as a Versatile Strategy for Polymeric Biomaterials Surface Modification: A Review", Biomacromolecules, 10(9), 2009, 2351-2378 (Year: 2009).*

(Continued)

*Primary Examiner* — James C Goloboy
(74) *Attorney, Agent, or Firm* — Nelson Mullins Riley & Scarborough LLP

(57) ABSTRACT

A method for making an insertable or implantable medical device including a lubricous coating on a silicone substrate includes treating the silicone substrate with an atmospheric plasma at about atmospheric pressure, the atmospheric plasma formed from a noble gas; applying a solution directly to the treated silicone substrate, the solution including a thermoplastic polyurethane; and heating the silicone substrate and the applied solution to form the lubricous coating on the silicone substrate.

16 Claims, 4 Drawing Sheets

(52) U.S. Cl.
CPC ....... *A61L 2420/02* (2013.01); *A61L 2420/06* (2013.01); *C08J 2383/04* (2013.01); *C08J 2483/10* (2013.01); *C08J 2487/00* (2013.01); *C10M 2217/0453* (2013.01); *C10N 2040/50* (2020.05); *C10N 2050/08* (2013.01)

(58) Field of Classification Search
CPC .............. A61L 2420/02; A61L 2420/06; C08J 2383/04; C08J 2483/10; C08J 2487/00; C01M 107/44; C01M 107/50; C01M 2217/0453; C01M 2219/025; C01N 2040/50; C01N 2050/08
See application file for complete search history.

(56) References Cited

U.S. PATENT DOCUMENTS

2006/0009829 A1    1/2006  Aron et al.
2017/0258966 A1*  9/2017  Kohama .............. C09D 133/26

OTHER PUBLICATIONS

Pellethane® 2363-55DE Tpu Technical Data Sheet, retrieved from the Internet at < https://www.lubrizol.com/-/media/Lubrizol/Health/TDS/Pellethane-2363-55DE.pdf> on Jun. 23, 21 (Year: 2017).*
International Search Report and Written Opinion issued in PCT/US2019/061375, dated Feb. 2, 2020, 13 pages.
Tim Desment et al., Nonthermal Plasma Technology as a Versatile Strategy for Polymeric Biomaterials Surface Modification: A Review, BIOMACROMOLECULES, vol. 10, No. 9, Published Sep. 2009, American Chemical Society, pp. 2351-2378.

* cited by examiner

LUBRICOUS SILICONE

CROSS-REFERENCE TO RELATED APPLICATION

This application claims priority to Provisional Application No. 62/768,607, filed Nov. 16, 2018, which is herein incorporated by reference in its entirety.

TECHNICAL FIELD

The present disclosure relates to implantable or insertable medical devices having a reduced friction. More specifically, the disclosure relates to silicone devices having a lubricous coating and methods of forming the same.

BACKGROUND

Silicone is commonly used in implantable or insertable medical devices because of silicone's desirable mechanical and biological properties. Silicone is flexible, durable, and biostable. However, silicone can have a tacky surface. When implanted in a patient, a medical device with a tacky silicone surface can contact body tissue and may result in tissue inflammation or abrasion of the silicone itself. Similarly, when inserted into a patient, a tacky silicone surface of a medical device can require a higher insertion force to overcome the tack, causing tissue inflammation or other damage.

For example, a medical electrical lead may include an outer insulating body for electrically insulating the conductor and allowing only the electrodes to make electrical contact with the body tissue. The outer lead body may be formed from silicone. The lead may be implanted by feeding the lead through a catheter system. It is desirable that the lead is lubricous enough to slide through the catheter system without sticking. Other implantable or insertable medical devices may include a silicone substrate that would benefit from a lubricous surface.

SUMMARY

Example 1 is a method for making an insertable or implantable medical device including a lubricous coating on a silicone substrate. The method includes treating the silicone substrate with an atmospheric plasma at about atmospheric pressure, the atmospheric plasma formed from a noble gas; applying a solution directly to the treated silicone substrate, the solution including a thermoplastic polyurethane; and heating the silicone substrate and the applied solution to form the lubricous coating on the silicone substrate.

Example 2 is the method of Example 1, wherein the noble gas includes at least one selected from the group of argon and helium.

Example 3 is the method of either of Examples 1 or 2, wherein the atmospheric plasma is a flow of plasma directed toward the silicone substrate.

Example 4 is the method of any of Examples 1-3, wherein the solution further includes at least one solvent selected from the group of dimethylformamide, dimethylacetamide tetrahydrofuran, trichloroethane, methylene chloride, cyclohexanone, cyclopentanone, dioxane, chloroform, tetrahydrofurfuryl alcohol, and benzyl alcohol.

Example 5 is the method of any of Examples 1-4, wherein the thermoplastic polyurethane includes at least one selected from the group of polycarbonate polyurethane, silicone polycarbonate polyurethane, a polyether polyurethane, and a silicone polyether urethane.

Example 6 is the method of Example 5, wherein the thermoplastic polyurethane is selected from the group consisting of polycarbonate polyurethane, silicone polycarbonate polyurethane, a polyether polyurethane, a silicone polyether urethane, and combinations thereof.

Example 7 is the method of any of Examples 1-6, wherein applying the solution directly to the silicone substrate includes spraying the solution onto the silicone substrate.

Example 8 is the method of any of Examples 1-6, wherein applying the solution directly to the silicone substrate includes dipping the silicone substrate into the solution.

Example 9 is the method of any of Examples 1-6, wherein applying the solution directly to the silicone substrate includes sponging the solution onto the silicone substrate.

Example 10 is the method of any of Examples 1-6, wherein applying the solution directly to the silicone substrate includes spinning the solution onto the silicone substrate.

Example 11 is the method of any of Examples 1-10, wherein heating the silicone substrate is at a temperature from 110° C. to 130° C. in air.

Example 12 is the method of any of Examples 1-11, wherein the silicone substrate is an outer surface of the medical device.

Example 13 is the method of any of Examples 1-12, wherein the silicone substrate is an inner surface of the medical device.

Example 14 is a medical device including a silicone substrate and a coating on the silicone substrate. The coating is made by any of the methods of Examples 1-13.

Example 15 is the medical device of Example 14, wherein the device is an electrical lead and the silicone substrate is an outer surface at a distal end of the electrical lead.

Example 16 is a method for making an insertable or implantable medical device including a lubricous coating on a silicone substrate. The method includes treating the silicone substrate with an atmospheric plasma at about atmospheric pressure, the atmospheric plasma formed from a gas consisting at least 98% by volume of a noble gas; applying a solution directly to the treated silicone substrate, the solution including a thermoplastic polyurethane; and heating the silicone substrate and the applied solution to form the lubricous coating on the silicone substrate.

Example 17 is the method of Example 16, wherein the noble gas includes at least one selected from the group of argon and helium.

Example 18 is the method of either of Examples 16 or 17, wherein the atmospheric plasma is a flow of plasma directed toward the silicone substrate.

Example 19 is the method of any of Examples 16-18, wherein the solution further includes at least one solvent selected from the group of dimethylformamide, dimethylacetamide tetrahydrofuran, trichloroethane, methylene chloride, cyclohexanone, cyclopentanone, dioxane, chloroform, tetrahydrofurfuryl alcohol, and benzyl alcohol.

Example 20 is the method of any of Examples 16-19, wherein the thermoplastic polyurethane includes at least one selected from the group of polycarbonate polyurethane, silicone polycarbonate polyurethane, a polyether polyurethane, and a silicone polyether urethane.

Example 21 is the method of any of Examples 16-20, wherein the thermoplastic polyurethane is selected from the group consisting of polycarbonate polyurethane, silicone polycarbonate polyurethane, a polyether polyurethane, a silicone polyether urethane, and combinations thereof.

Example 22 is the method of any of Examples 16-21, wherein applying the solution directly to the silicone substrate includes spraying the solution onto the silicone substrate.

Example 23 is the method of any of Examples 16-21, wherein applying the solution directly to the silicone substrate includes dipping the silicone substrate into the solution.

Example 24 is the method of Examples 16-21, wherein applying the solution directly to the silicone substrate includes sponging the solution onto the silicone substrate.

Example 25 is the method of any of Examples 16-21, wherein applying the solution directly to the silicone substrate includes spinning the solution onto the silicone substrate.

Example 26 is the method of any of Examples 16-25, wherein heating the silicone substrate is at a temperature from 110° C. to 130° C. in air.

Example 27 is the method of any of Examples 16-26, wherein the silicone substrate is an outer surface of the medical device.

Example 28 is the method of any of Examples 16-26, wherein the silicone substrate is an inner surface of the medical device.

Example 29 is a medical device including a silicone substrate and a lubricous coating disposed directly on the silicone substrate, the coating including a thermoplastic polyurethane.

Example 30 is the medical device of Example 29, wherein the thermoplastic polyurethane includes at least one selected from the group of polycarbonate polyurethane, silicone polycarbonate polyurethane, a polyether polyurethane, and a silicone polyether urethane.

Example 31 is the medical device of either of Examples 29 and 30, wherein the thermoplastic polyurethane is selected from the group consisting of polycarbonate polyurethane, silicone polycarbonate polyurethane, a polyether polyurethane, a silicone polyether urethane, and combinations thereof.

Example 32 is the medical device of any of Examples 29-31, wherein the silicone substrate is an outer surface of the medical device.

Example 33 is the medical device of any of Examples 29-31, wherein the silicone substrate is an inner surface of the medical device.

Example 34 is the medical device of any of Examples 29-31, wherein the device is an electrical lead and the silicone substrate is an outer surface at a distal end of the electrical lead.

Example 35 is the medical device of any of Examples 29-31, wherein the device is a catheter and the silicone substrate is an outer surface of the catheter.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
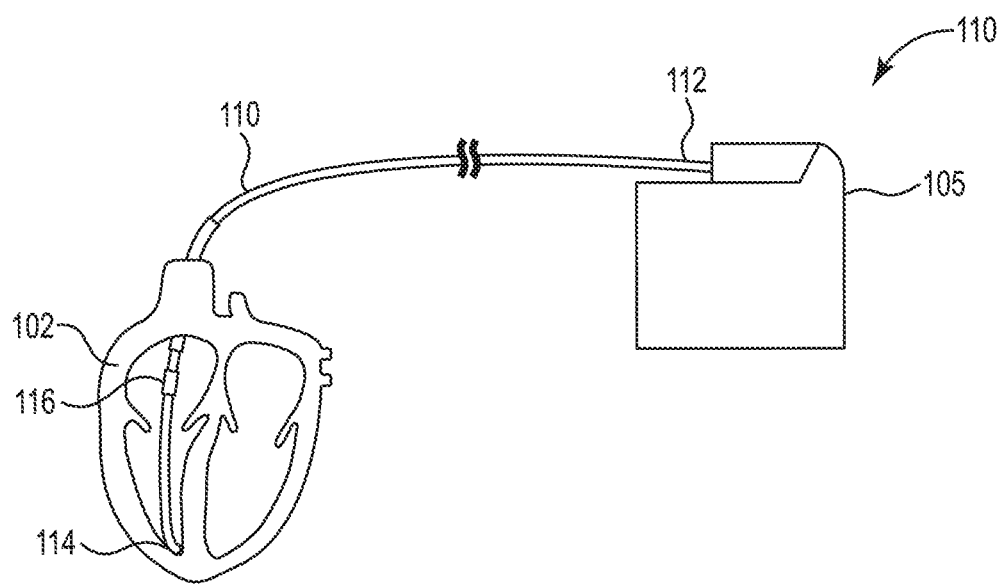
FIG. 1 is a schematic illustration of a medical electrical device, according to some embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

An implantable or insertable medical device may include a silicone substrate. As described herein, a coating may be formed on at least a portion of the silicone substrate to provide a surface with lubricous coating to reduce both static and dynamic friction. In some embodiments, the coating may completely cover or surround the silicone substrate. The coating may be formed by treating the silicone substrate with an atmospheric plasma formed from a noble gas, and then applying a thermoplastic polyurethane solution directly to the treated silicone substrate. The coated silicone substrate may be baked or allowed to air dry to form a lubricous coating on the silicone substrate.

A plasma is a gas in which a significant percentage of the atoms or molecules are ionized. Generally, plasmas are formed within vacuum chambers under sub-atmospheric conditions because the lower pressures permit the plasmas to be generated using a variety of gases, such as oxygen or nitrogen, which may be difficult to ionize at higher pressures. An atmospheric plasma may be created as a flow, or jet, of noble gas is ionized at about atmospheric pressure without the use of a vacuum chamber. As used herein, about atmospheric pressure means normal atmospheric pressure plus any increase in local pressure due to the flow of the noble gas which must be somewhat above atmospheric pressure in order to flow.

An atmospheric plasma may be more efficient compared to a sub-atmospheric plasma because there is no need to pump down a vacuum chamber before use, and then vent the vacuum chamber after use, saving time and energy. An atmospheric plasma also does not require the capital investment or maintenance associated with a vacuum chamber and its attendant vacuum pumps, filters, traps, and vacuum instrumentation.

It has been found that a thermoplastic polyurethane coating formed on a silicone substrate treated with an atmospheric plasma formed from a noble gas according to this disclosure is not only lubricous, but is also durable, bonding tenaciously to the silicone substrate. The lubricous coating is bonded directly to the silicone substrate without the need for an intervening tie layer or the need for complex chemistry to create functional groups on the silicone substrate. It has also been found that a thermoplastic polyurethane coating formed on a silicone substrate without the atmospheric plasma formed from a noble gas according to this disclosure does not adhere well to the silicone substrate and easily rubs off. Without wishing to be bound by any theory, it is believed that the atmospheric plasma removes low-molecular weight materials from the surface of the silicone substrate and creates a thin, cross-linked silica-like surface layer, rendering the surface receptive to bonding with the thermoplastic polyurethane.

The lubricous coatings as described herein are not hydrogels. Thus, they may provide lubricity under dry conditions. Hydrogels also swell when exposed to water, requiring a lead or medical device coated with a hydrogel to be smaller in diameter to use a given delivery mechanism. The lubricous coatings as described herein are believed to be more durable than hydrogels.

Implantable or insertable medical devices suitable for use with the lubricious coatings disclosed herein can include devices such as catheters, shunts, heart pumps, male incontinence devices, erectile restoration devices, ostomy ports, gastric balloons, bladder devices, breast implants, intubation tubes, guide wires, medical electrical leads, and medical electrical devices for use with medical electrical leads, for example.

Medical electrical devices can include implantable electrical stimulation systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), cardiac resynchronization and defibrillation (CRDT) devices, and subcutaneous implantable cardioverter-defibrillators (SICD's), for example.

FIG. 1 is a schematic illustration of a medical electrical device 100 for delivering and/or receiving electrical pulses or signals to stimulate, shock, and/or sense a heart 102. The device 100 may include pulse generator 105 and an electrical lead 110. The pulse generator 105 may include a source of power as well as an electronic circuitry portion (not shown). Optionally, the electronic circuitry can include one or more microprocessors that provide processing and/or evaluation functions, and that can determine and deliver electrical shocks or pulses of different energy levels and timing. The pulse generator 105 can be employed as part of a variety of useful therapies, including for neurostimulation, ventricular defibrillation and/or cardioversion. In the case of ventricular defibrillation and/or cardioversions, it can also be used to pace the heart in response to one or more sensed cardiac arrhythmia including fibrillation, cardiac resynchronization, tachycardia, or bradycardia. The pulse generator 105 can be powered by one or more batteries, though any other internal or external power source may be used for the given application. The pulse generator 105 may sense intrinsic signals of the heart 102 and generate a series of timed electrical discharges or pulses.

The pulse generator 105 may be generally implanted into a subcutaneous pocket made in the wall of the chest. Alternatively, the pulse generator 105 may be placed in a subcutaneous pocket made in the abdomen, or in another location. It should be noted that while the electrical lead 110 is illustrated for use with a heart, the electrical lead 110 is suitable for other forms of electrical stimulation/sensing as well.

As shown in FIG. 1, the electrical lead 110 can extend from a proximal end 112, where it is coupled with the pulse generator 105 to a distal end 114, where it coupled with a portion of the heart 102, when implanted or otherwise coupled therewith. Also disposed along at least a portion of the electrical lead 110, for example near the distal end 114, is at least one electrode 116. The electrode 116 electrically couples the electrical lead 110 with the heart 102 and allows for electrical signals to be delivered from the pulse generator 105 to the target tissue or location. At least one electrical conductor (not shown) is disposed within electrical lead 110 and extends generally from the proximal end 112 to the distal end 114 of the electrical lead 110. The at least one electrical conductor electrically couples the electrode 116 with the proximal end 112 of the electrical lead 110. The electrical conductor carries electrical current and pulses between the pulse generator 105 and the electrode 116, and to and from the heart 102. In one option, the at least one electrical conductor is a coiled conductor. In another option, the at least one electrical conductor includes one or more cables.

During implantation, the electrical lead 110 may be inserted through tissue and body lumens until the distal end 114 and electrode 116 are suitably disposed for effective therapy. Once implanted, the electrical lead 110 may be in continuous or intermittent contact with body tissues. During implantation and once implanted, it is beneficial for at least the distal end 114 of the electrical lead 110 to have a lubricous surface as described below to reduce any inflammation of, or damage to, body tissues.

Figure 2:
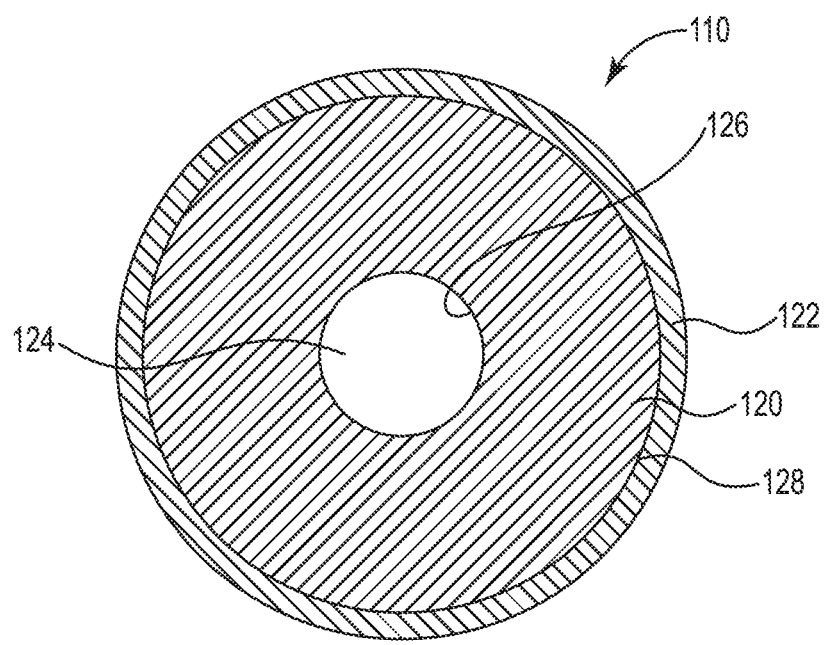
FIG. 2 is schematic cross-sectional view of a distal end of an electrical lead of FIG. 1, according to some embodiments of this disclosure.

FIG. 2 is schematic cross-sectional view of a distal end 114 of the electrical lead 110 of FIG. 1, according to some embodiments of this disclosure. As shown in FIG. 2, the electrical lead 110 may include a lead body 120, a lubricous coating 122, and a lumen 124. The lead body 120 may include an inner surface 126 and an outer surface 128. The inner surface 126 forms the lumen 124. The lead body 120 may extend the length of the electrical lead 110 from the proximal end 112 to the distal end 114. The lumen 124 is a channel extending axially through the lead body 120. Although only one lumen 124 is shown, it is understood that the lead body 120 may include more than one lumen 124 extending axially thorough the lead body.

The lead body 120 can be flexible, but is generally non-compressible along its length. The lead body 120 can have a substantially circular cross-section, as shown in FIG. 2. The at least one electrical conductor (not shown) may extend through the lumen 124 such that the lead body 120 can isolate the electrical conductor from the surrounding tissue or environment.

The lead body 120 can be formed, at least in part, of silicone. The lead body 120 at the distal end 114 may be formed entirely of silicone, as shown in FIG. 2. The lead body 120 may be formed entirely of silicone from the proximal end 112 to the distal end 114. The composition of the lead body 120 may be substantially uniform along its length, or it may vary in composition along it length, along its width, or along its length and width. The outer surface 128 may be a silicone substrate upon which the lubricous coating 122 is formed.

The lubricous coating 122 may be disposed on at least a portion of the outer surface 128. The lubricous coating 122 may extend along a portion of the length of the lead body 120, or along the length of the entire lead body 120 from the proximal end 112 to the distal end 114. The lubricous coating 122 may radially surround the lead body 120, as shown in FIG. 2. The lubricous coating 122 is disposed directly on the outer surface 128 of the lead body 120. That is, there is no intervening layer, such as a tie layer between the lubricous coating 122 and the lead body 120.

The lubricous coating 122 may be a conformal coating on the outer surface 128 of the lead body 120. That is, the lubricous coating 122 may conform to the topography of the outer surface 128. The lubricous coating 122 may have a radially and/or axially uniform composition and/or thickness.

The lubricious coating 122 may have a thickness as small as 0.001 mm, 0.002 mm, 0.005 mm, 0.01 mm, 0.02 mm, or 0.05 mm, or as large as 0.1 mm, 0.2 mm, 0.5 mm, 1 mm, 1.5 mm, or 2 mm, or be within any range defined between any two of the foregoing values, such as 0.001 mm to 2 mm, 0.002 mm to 1.5 mm, 0.005 mm to 1 mm, 0.01 mm to 0.5 mm, 0.02 mm to 0.2 mm, 0.05 mm to 0.1 mm, or 0.1 mm to 0.2 mm, for example.

The lubricous coating 122 may include a thermoplastic polyurethane. The thermoplastic polyurethane may include at least one selected from the group of polycarbonate polyurethane, silicone polycarbonate polyurethane, a polyether polyurethane, and a silicone polyether urethane. The thermoplastic polyurethane may be selected from the group consisting of polycarbonate polyurethane, silicone polycarbonate polyurethane, a polyether polyurethane, and a silicone polyether urethane, or combinations thereof.

Examples of polycarbonate polyurethanes include Carbothane™ from Lubrizol, Wickliffe, Ohio, Bionate® from DSM Biomedical, Exton, Pa., and ChronoFlex C® and ChronoFlex AL® from AdvanSource Biomaterials Corp., Wilmington, Mass. Examples of silicone polycarbonate polyurethanes include CarboSil® 20 from DSM Biomedical, Exton, Pa. and ChronoSil AL® from AdvanSource Biomaterials Corp., Wilmington, Mass. An example of a silicone polyether polyurethane is PurSil® from DSM Biomedical, Exton, Pa.

As describe further herein, the lubricous coating 122 may reduce the frictional force experienced when the electrical lead 110 is moved within a patient, or upon insertion through a medical system, such as a catheter system. Friction forces include dynamic friction and static friction. Dynamic (or kinetic) friction occurs between two objects that are moving relative to one another, and static friction occurs between two objects that are not moving relative to one another. The lubricous coating 122 may reduce the dynamic friction force and the static friction force of the electrical lead 110, compared to the uncoated silicone lead body 120.

Figure 3:
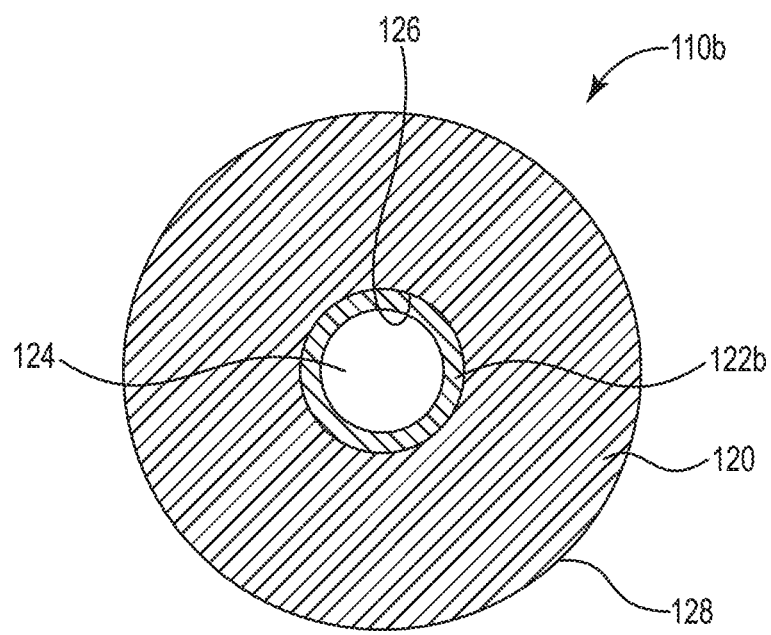
FIG. 3 is schematic cross-sectional view of a distal end of the electrical lead of FIG. 1, according to some other embodiments of this disclosure.

FIG. 3 is schematic cross-sectional view of the distal end 114 of an electrical lead 110b. The electrical lead 110b is identical to the electrical lead 110 of FIGS. 1 and 2, except that instead of a lubricous coating 122 disposed on the outer surface 128, the electrical lead 110b includes a lubricous coating 122b disposed on the inner surface 126. The lubricous coating 122b may be as described above for the lubricous coating 122 in reference to FIG. 2.

So disposed, the lubricous coating 122b may improve the lubricity (i.e. reduce the static and dynamic frictional forces) of the inner surface 126 compared to the uncoated inner surface 126. The improved lubricity may reduce the force required to install the electrical conductor into and through the lumen 124. The improved lubricity may also reduce the abrasion of the inner surface 126 from the movement of the electrical conductor within the lumen 124 as the electrical lead flexes from the movement of body tissues during use.

Thus, the silicone substrate upon which the lubricous coating 122 or the lubricous coating 122b is disposed may be the outer surface 128 of the lead body 120, as shown in FIG. 2 or an inner surface 126 of the lead body 120, as shown in FIG. 3, respectively. Alternatively, the lubricous coating 122 may be disposed on the outer surface 128 and the lubricous coating 122b may be disposed on the inner surface 126 of the same lead body 120.

A method for making an insertable or implantable medical device including a lubricous coating on a silicone substrate includes treating the silicone substrate with an atmospheric plasma, as described above. The atmospheric plasma may be formed from a noble gas, such as helium, neon, argon, or any combination thereof. The concentration of noble gas in the atmospheric plasma by volume may be greater than 98%, 99%, or 99.5%, or within any range defined between any two of the foregoing values. The atmospheric plasma may be formed exclusively from a noble gas.

The medical device can be treated by moving and/or rotating the medical device through the flow, or jet, of the atmospheric plasma. One example of a device for creating the atmospheric plasma suitable for treating the silicone substrate of the medical device according to this disclosure is a PT-2000P Duradyne Plasma Treatment System from Tri-Star Technologies, El Segundo, Calif.

Once the silicone substrate is treated, a solution including a thermoplastic polyurethane is applied directly to the treated silicone substrate. The thermoplastic polyurethane may be any of those described above in reference to FIG. 2. The solution may include at least one solvent selected from the group of dimethylformamide, dimethylacetamide tetrahydrofuran, trichloroethane, methylene chloride, cyclohexanone, cyclopentanone, dioxane, chloroform, tetrahydrofurfuryl alcohol, benzyl alcohol, n-butanol, t-butanol, phenoxyethanol, benzyl benzoate, butyl benzoate, butyl diglycol acetate, caprolactone (epsilon), dimethyl isosorbide, ethylene carbonate, ethylene glycol 2-ethylhexyl ether, fatty acid methyl ester, glycerol carbonate, glycerol diacetate, glycerol triacetate, hexylene glycol, methyl oleate, propylene carbonate, propylene glycol, propylene glycol phenyl ether, sulfolane, texanol, and tributyl phosphate. The solution may consist of the thermoplastic polyurethane in solution with a solvent selected from the group consisting of dimethylformamide, dimethylacetamide tetrahydrofuran, trichloroethane, methylene chloride, cyclohexanone, cyclopentanone, dioxane, chloroform, tetrahydrofurfuryl alcohol, benzyl alcohol, n-butanol, t-butanol, phenoxyethanol, benzyl benzoate, butyl benzoate, butyl diglycol acetate, caprolactone (epsilon), dimethyl isosorbide, ethylene carbonate, ethylene glycol 2-ethylhexyl ether, fatty acid methyl ester, glycerol carbonate, glycerol diacetate, glycerol triacetate, hexylene glycol, methyl oleate, propylene carbonate, propylene glycol, propylene glycol phenyl ether, sulfolane, texanol, and tributyl phosphate and combinations thereof.

The solution may be applied by spraying the solution onto the silicone substrate. The solution may be applied by sponging the solution onto the silicone substrate. The solution may be applied by spinning the solution onto the silicone substrate. The solution may be applied by dipping the silicone surface into the solution.

The solution may be applied at room temperature, or at an elevated temperature to enhance processing for more viscous solutions having higher concentrations of thermoplastic polyurethane and/or thermoplastic polyurethanes of high molecular weight. The elevated temperature may be as low as 30° C., 35° C., 40° C., 45° C., 50° C., 55° C., or 60° C., or as high as 65° C., 70° C., 75° C., 80° C., 85° C., 90° C., 95° C., or 100° C., or be within any range defined between any two of the foregoing values, such as 30° C. to 100° C., 35° C. to 95° C., 40° C. to 90° C., 45° C. to 85° C., 50° C.

to 80° C., 55° C. to 75° C., 60° C. to 70° C., 30° C. to 50° C., or 30° C. to 40° C., for example.

It has been found that a time delay between the plasma treatment of the silicone substrate and the subsequent application of the solution to the silicone substrate does not result in a significant reduction in the adhesion of the lubricious coating to the silicone substrate for delays as great as 24 hours.

Once the solution has been applied to the silicone surface, the silicone substrate with the applied solution may be exposed to air at room temperature to allow the one or more solvents to evaporate, thus forming the lubricious coating. However, it has been found that while exposure to room-temperature air evaporates the one or more solvents, it may result in an inconsistent coating should the solution pool and settle along the silicone substrate. Alternatively, or additionally, the silicone substrate with the applied solution may be heated to drive off the one or more solvents more quickly, forming a more consistent lubricious coating. The heating can be by baking in an oven, heating with a heat gun, and/or by exposure to infrared radiation. Heating in an oven can include by natural convection and/or forced convection. The heating may be in air or an inert atmosphere.

The silicone substrate with the applied solution may be heated to a temperature as low as 30° C., 40° C., 60° C., 80° C., or 100° C., or to a temperature as high as about 120° C., 140° C., 160° C., 180° C., or 200° C., or to a temperature within any range defined between any two of the foregoing values, such as 30° C. to 200° C., 40° C. to 180° C., 60° C. to 160° C., 80° C. to 140° C., 100° C. to 120° C. or 100° C. to 140° C., for example.

Although the method described above provides the lubricious coating from a single application of the solution to the silicone substrate, it is understood that the process steps of applying the solution and heating the solution may be repeated to obtain a thicker lubricous coating.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

EXAMPLES

Example 1—Manufacture of a Lubricous Silicone Polycarbonate Polyurethane Coating on a Silicone Substrate—CarboSil® 0.04 g/ml In this Example, the manufacture of a lubricous silicone polycarbonate polyurethane coating on a silicone substrate as described above is demonstrated. A silicone polycarbonate polyurethane, CarboSil® 55D, was dissolved in dimethylformamide at 60° C. to form a solution having a concentration of 0.0402 grams of silicone polycarbonate polyurethane per milliliter of dimethylformamide. The solution was cooled to room temperature. A silicone substrate was treated for 60 seconds with an atmospheric plasma formed from argon gas at 70 watts. The plasma treatment system was a PT-2000P Duradyne Plasma Treatment System. Within about 10 seconds, the solution was applied the treated silicone substrate by dipping the silicone substrate into the solution and then removing the silicone substrate from the solution. The silicone substrate with the applied solution was baked in an oven at 120° C. for 10 minutes in ambient air to form the lubricous silicone polycarbonate polyurethane coating on the silicone substrate.

Example 2—Manufacture of a Lubricous Silicone Polycarbonate Polyurethane Coating on a Silicone Substrate—CarboSil® 0.08 g/ml In this Example, the manufacture of another lubricous silicone polycarbonate polyurethane coating on a silicone substrate as described above is demonstrated. A silicone polycarbonate polyurethane, CarboSil® 55D, was dissolved in dimethylformamide at 60° C. to form a solution having a concentration of 0.0826 grams of silicone polycarbonate polyurethane per milliliter of dimethylformamide. The solution was cooled to room temperature. A silicone substrate was treated for 60 seconds with an atmospheric plasma formed from argon gas at 70 watts. The plasma treatment system was a PT-2000P Duradyne Plasma Treatment System. Within about 10 seconds, the solution was applied the treated silicone substrate by dipping the silicone substrate into the solution and then removing the silicone substrate from the solution. The solution was at room temperature. The silicone substrate with the applied solution was baked in an oven at 120° C. for 10 minutes in ambient air to form the lubricous silicone polycarbonate polyurethane coating on the silicone substrate.

Example 3—Manufacture of a Lubricous Silicone Polycarbonate Polyurethane Coating on a Silicone Substrate—ChronoSil AL® 0.08 g/ml In this Example, the manufacture of a lubricous silicone polycarbonate polyurethane coating on a silicone substrate as described above is demonstrated. Another silicone polycarbonate polyurethane, ChronoSil AL® 5D, was dissolved in dimethylformamide at room temperature to form a solution having a concentration of 0.0814 grams of silicone polycarbonate polyurethane per milliliter of dimethylformamide. A silicone substrate was treated for 60 seconds with an atmospheric plasma formed from argon gas at 70 watts. The plasma treatment system was a PT-2000P Duradyne Plasma Treatment System. Within about 10 seconds, the solution was applied the treated silicone substrate by dipping the silicone substrate into the solution and then removing the silicone substrate from the solution. The solution was at room temperature. The silicone substrate with the applied solution was baked in an oven at 120° C. for 10 minutes in ambient air to form the lubricous silicone polycarbonate polyurethane coating on the silicone substrate.

Example 4—Manufacture of a Lubricous Silicone Polycarbonate Polyurethane Coating on a Silicone Substrate—ChronoSil AL® 0.08 g/ml Double Dip In this Example, the manufacture of a lubricous silicone polycarbonate polyurethane coating on a silicone substrate as described above is demonstrated. A silicone substrate was treated for 60 seconds with an atmospheric plasma formed from argon gas at 70 watts. The plasma treatment system was a PT-2000P Duradyne Plasma Treatment System. Within about 10 seconds, the solution of Example 3 was applied the treated silicone substrate by dipping the silicone substrate into the solution and then removing the silicone substrate from the solution. The solution was at room temperature. The silicone substrate with the applied solution was baked in an oven at 120° C. for 10 minutes in ambient air. Following the bake, the coated silicone substrate was again dipped into the room temperature solution and then removed from the solution. The silicone substrate was again baked in an oven at 120° C. for 10 minutes in ambient air to form the lubricous silicone polycarbonate polyurethane coating on the silicone substrate.

Example 5—Manufacture of a Lubricous Polycarbonate Polyurethane Coating on a Silicone Substrate—ChronoFlex C® 0.1 g/ml In this Example, the manufacture of a lubricous polycarbonate polyurethane coating on a silicone substrate as described above is demonstrated. A polycarbonate polyurethane, ChronoFlex® C 55D, was dissolved in dimethylacetamide at room temperature to form a solution having a concentration of 0.0814 grams of silicone polycarbonate polyurethane per milliliter of dimethylacetamide. A silicone substrate was treated for 60 seconds with an atmospheric plasma formed from argon gas at 70 watts. The plasma treatment system was a PT-2000P Duradyne Plasma Treatment System. Within about 10 seconds, the solution was applied the treated silicone substrate by dipping the silicone substrate into the solution and then removing the silicone substrate from the solution. The solution was at room temperature. The silicone substrate with the applied solution was baked in an oven at 120° C. for 10 minutes in ambient air to form the lubricous polycarbonate polyurethane coating on the silicone substrate.

Example 6—Manufacture of a Lubricous Polycarbonate Polyurethane Coating on a Silicone Substrate—ChronoFlex C® 0.1 g/ml Double Dip In this Example, the manufacture of a lubricous polycarbonate polyurethane coating on a silicone substrate as described above is demonstrated. A silicone substrate was treated for 60 seconds with an atmospheric plasma formed from argon gas at 70 watts. The plasma treatment system was a PT-2000P Duradyne Plasma Treatment System. Within about 10 seconds, the solution of Example 5 was applied the treated silicone substrate by dipping the silicone substrate into the solution and then removing the silicone substrate from the solution. The solution was at room temperature. The silicone substrate with the applied solution was baked in an oven at 120° C. for 10 minutes in ambient air. Following the bake, the coated silicone substrate was again dipped into the solution at room temperature and then removed from the solution. The silicone substrate was again baked in an oven at 120° C. for 10 minutes in ambient air to form the lubricous polycarbonate polyurethane coating on the silicone substrate.

Example 7—Manufacture of a Lubricous Polycarbonate Polyurethane Coating on a Silicone Substrate at Elevated Temperature—ChronoFlex C® 0.1 g/ml In this Example, the manufacture of a lubricous polycarbonate polyurethane coating on a silicone substrate as described above is demonstrated. A silicone substrate was treated for 60 seconds with an atmospheric plasma formed from argon gas at 70 watts. The plasma treatment system was a PT-2000P Duradyne Plasma Treatment System. Within about 10 seconds, the solution was applied the treated silicone substrate by dipping the silicone substrate into the solution of Example 5 and then removing the silicone substrate from the solution. The solution was at 80° C. The silicone substrate with the applied solution was baked in an oven at 120° C. for 10 minutes in ambient air to form the lubricous polycarbonate polyurethane coating on the silicone substrate.

Test Results of Lubricous Coatings on a Silicone Substrate

Figure 4:
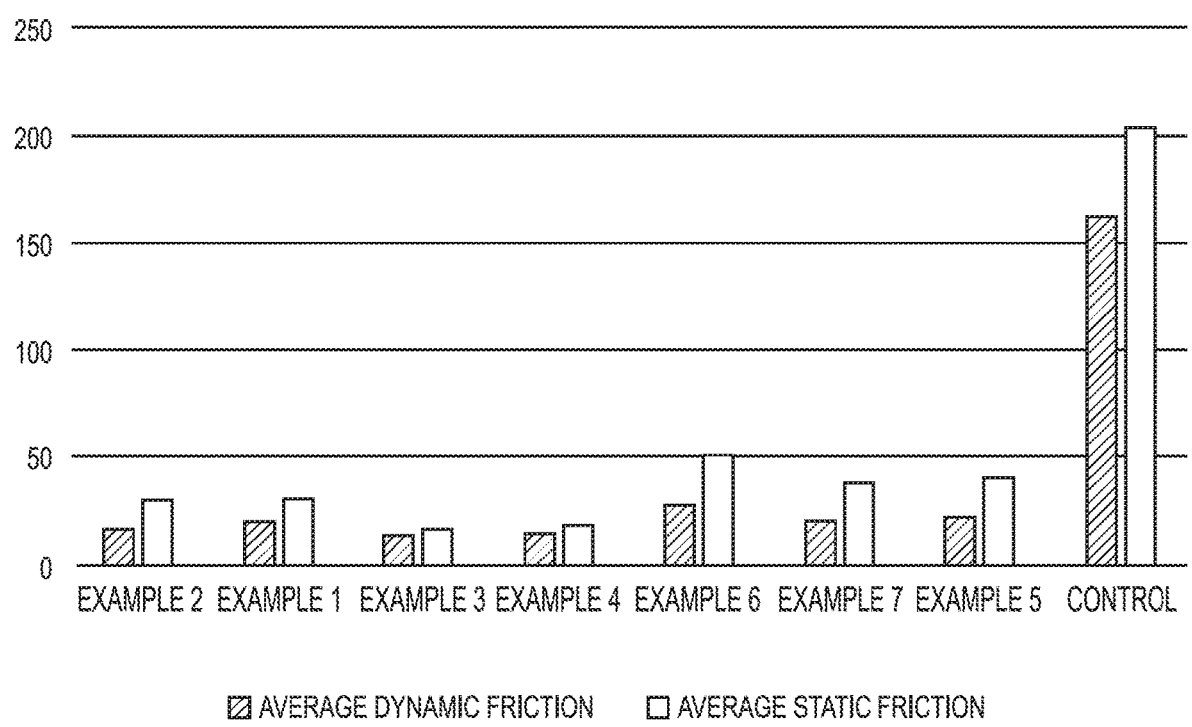
FIG. 4 illustrates the reduction in static and dynamic friction force on PTFE of silicone test samples coated with different thermoplastic urethane coatings, according to some embodiments of this disclosure.
Figure 5:
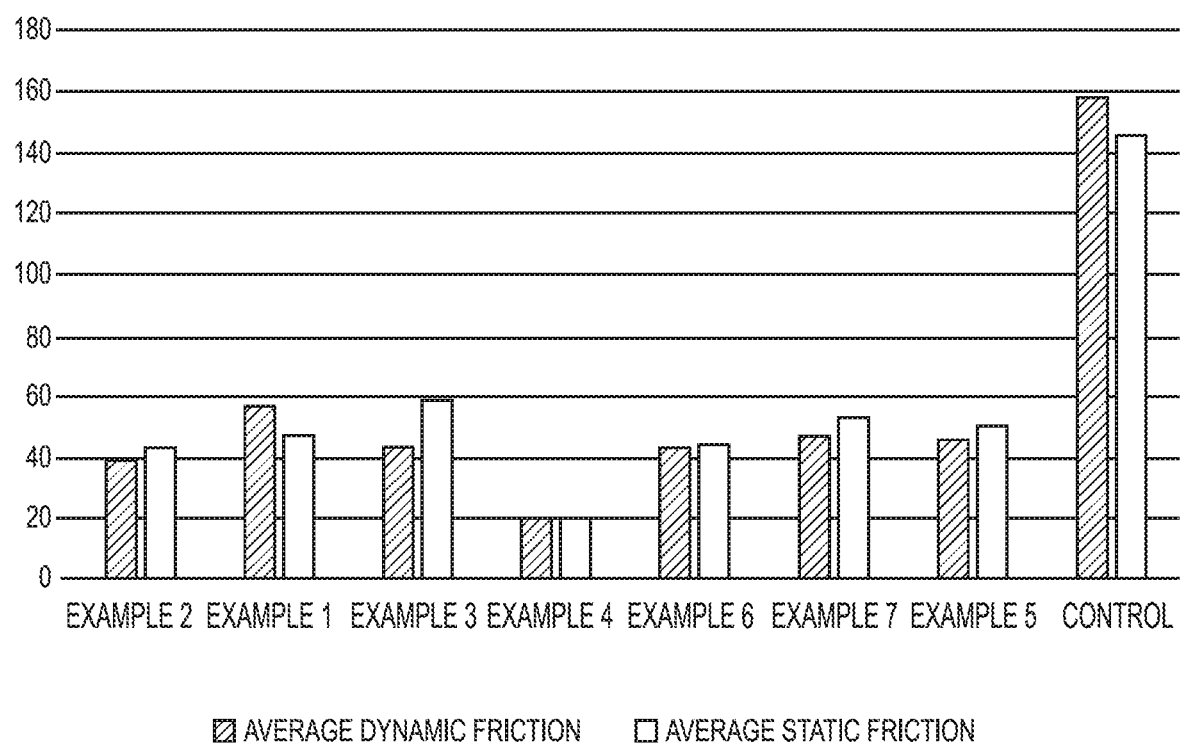
FIG. 5 illustrates the reduction in static and dynamic friction force on stainless steel of silicone test samples coated with different thermoplastic urethane coatings, according to some embodiments of this disclosure.

Substrates from each of the Examples described above were evaluated on a sled style friction tester to compare reductions in dynamic and static friction relative to an uncoated silicone substrate. The tester was a Hanatek Advanced Friction Tester. FIG. 4 illustrates the relative static and dynamic friction force of the substrates when pulled over a polytetrafluoroethylene (PTFE) surface. FIG. 5 illustrates the relative static and dynamic friction force of the substrates when pulled over a stainless-steel surface. As shown in FIG. 4, the silicone substrates with lubricous coatings according to this disclosure had an 83% to 92% reduction in the dynamic friction force and a 75% to 92% reduction in the static friction force when pulled over the PTFE surface compared to the uncoated silicone substrate (control). Similarly, as shown in FIG. 5, the silicone substrates with lubricous coatings according to this disclosure had a 64% to 87% reduction in the dynamic friction force and a 59% to 86% reduction in the static friction force when pulled over the stainless-steel surface compared to the uncoated silicone substrate (control).

As shown most clearly in FIG. 5, comparing Example 1 to Example 2, it appears that increasing the concentration of thermoplastic polyurethane in the solution may produce a coating having lower dynamic and static friction. Comparing Example 3 to Example 4, and comparing Example 5 to Example 6, it appears that dipping and baking the silicone substrate twice, instead of just once, may produce a coating having lower dynamic and static friction.

We claim:

1. A method for making an insertable or implantable medical device including a lubricous coating on a silicone substrate, the method comprising:
    treating the silicone substrate with an atmospheric plasma at about atmospheric pressure, the atmospheric plasma formed from a gas consisting at least 98% by volume of a noble gas;
    applying a solution directly to the treated silicone substrate, the solution including a thermoplastic polyurethane; and
    heating the silicone substrate and the applied solution to form the lubricous coating on the silicone substrate.

2. The method of claim 1, wherein the noble gas includes at least one selected from the group of argon and helium.

3. The method of claim 1, wherein the atmospheric plasma is a flow of plasma directed toward the silicone substrate.

4. The method of claim 1, wherein the solution further includes at least one solvent selected from the group of dimethylformamide, dimethylacetamide tetrahydrofuran, trichloroethane, methylene chloride, cyclohexanone, cyclopentanone, dioxane, chloroform, tetrahydrofurfuryl alcohol, and benzyl alcohol.

5. The method of claim 1, wherein the thermoplastic polyurethane includes at least one selected from the group of polycarbonate polyurethane, silicone polycarbonate polyurethane, a polyether polyurethane, and a silicone polyether urethane.

6. The method of claim 1, wherein the thermoplastic polyurethane is a silicone polycarbonate polyurethane.

7. The method of claim 1, wherein applying the solution directly to the silicone substrate includes spraying the solution onto the silicone substrate.

8. The method of claim 1, wherein applying the solution directly to the silicone substrate includes dipping the silicone substrate into the solution.

9. The method of claim 1, wherein applying the solution directly to the silicone substrate includes sponging the solution onto the silicone substrate.

10. The method of claim 1, wherein applying the solution directly to the silicone substrate includes spinning the solution onto the silicone substrate.

11. The method of claim 1, wherein heating the silicone substrate is at a temperature from 110° C. to 130° C. in air.

12. The method of claim 1, wherein the silicone substrate is an outer surface of the medical device.

13. The method of claim 1, wherein the silicone substrate is an inner surface of the medical device.

14. A medical device comprising:
    a silicone substrate; and
    a lubricous coating disposed directly on the silicone substrate, the coating including a thermoplastic polyurethane, wherein the device is an electrical lead and the silicone substrate is an outer surface at a distal end of the electrical lead.

15. The medical device of claim 14, wherein the thermoplastic polyurethane includes at least one selected from the group of polycarbonate polyurethane, silicone polycarbonate polyurethane, a polyether polyurethane, and a silicone polyether urethane.

16. The medical device of claim 14, wherein the thermoplastic polyurethane is a silicone polycarbonate polyurethane.

* * * * *